United States Patent [19]
Chen et al.

[11] Patent Number: 4,496,730
[45] Date of Patent: Jan. 29, 1985

[54] PHOSPHOROUS DIKETONATE ELECTRON ACCEPTING RING COMPOUNDS AS SENSITIZERS FOR ELECTRON DONATING PHOTOCONDUCTIVE COMPOSITIONS

[75] Inventors: Chin H. Chen; Thomas E. Goliber; Jerome H. Perlstein; George A. Reynolds, all of Rochester, N.Y.

[73] Assignee: Eastman Kodak Company, Rochester, N.Y.

[21] Appl. No.: 420,461

[22] Filed: Sep. 20, 1982

[51] Int. Cl.$^3$ .............................. C07F 9/21; C07F 9/58
[52] U.S. Cl. ..................................... 546/23; 260/936; 260/937; 548/113; 548/119; 430/83
[58] Field of Search .................. 260/936, 937; 546/23; 548/113, 119; 542/412

[56] References Cited

U.S. PATENT DOCUMENTS 2,556,515 6/1951 Brooker et al. ................... 260/240.7
3,678,045 7/1972 Van Hare et al. ................. 260/240.4
4,365,017 12/1982 Detty et al. ........................... 430/83

FOREIGN PATENT DOCUMENTS 625347 6/1949 United Kingdom .
633873 12/1949 United Kingdom .
647542 12/1950 United Kingdom .
649725 1/1951 United Kingdom .
1199794 7/1970 United Kingdom .

OTHER PUBLICATIONS

Research Disclosure, Item 17643, Dec. 1978, p. 23.
"Synthesis of Tetrafluoro (Pentane-2,4-Dionato) Phosphorous (V) and Analogous Compounds" Brown & Bladon Chemical Communications of 1966, p. 304.

Primary Examiner—Richard L. Raymond
Attorney, Agent, or Firm—John R. Everett

[57] ABSTRACT

Phosphorous diketonate electron accepting compounds are disclosed for use as sensitizers in electron donating photoconductive compositions. Methine dyes having a phosphorous diketonate component and a method of making same are also disclosed.

7 Claims, No Drawings

PHOSPHOROUS DIKETONATE ELECTRON ACCEPTING RING COMPOUNDS AS SENSITIZERS FOR ELECTRON DONATING PHOTOCONDUCTIVE COMPOSITIONS

FIELD OF THE INVENTION

This invention relates to a novel method of making phosphorous diketonate compounds, novel methine dye compounds comprising a phosphorous diketonate component and the use of phosphorous diketonate compounds as electron acceptors in electron donating photoconductive compositions and elements.

BACKGROUND OF THE INVENTION

Ring compounds comprising an inorganic atom in association with a diketonate structure are known. For example, some, such as boron diketonates, are known to be useful as electron accepting sensitizers in electron donating photoconductive compositions. On the other hand, others such as tin and copper diketonate compounds have no practical utility in sensitizing electron donating photoconductors.

Brown and Bladon describes the synthesis of three different phosphorous diketonate compositions in their publication "Synthesis of Tetrafluoro(pentane-2,4-dionato)phosphorous(V) and Analogous Compounds" appearing in *Chemical Communications* of 1966, page 304. However, this method is useful in making only a limited number of compounds. For example, the method does not describe the preparation of methine dyes having a phosphorous diketonate component.

Commonly assigned, U.S. patent application Ser. No. 279,365 filed July 1, 1981 by Detty et al, now U.S. Pat. No. 4,365,017, granted Dec. 21, 1982 discloses telluropyrylium compounds which include a tetrafluorophosphorous diketonate component for use in improving the quantum efficiency and sensitvity of electron donating photoconductive compositions. However, this application does not describe a method that could be used to make tellurium-free phosphorous diketonates.

Although boron diketonate compounds do improve the quantum efficiency and the sensitivity of electron donating photoconductive compositions above about 600 nm in wavelength, the resultant quantum efficiency and photosensitivity could be improved.

SUMMARY OF THE INVENTION

The present invention provides a method for making novel methine dyes having a tetrafluorophosphorus diketonate ring component including ring components in which one of the oxygen components of the ring have been replaced by sulfur or substituted nitrogen. The present invention also provides photoconductive compositions comprising tellurium-free tetrafluorophosphorous diketonate compounds as sensitizers. The compounds are useful in improving the quantum efficiency and photosensitivity of electron donating photoconductive compositions. They also improve the performance of photoconductive compositions containing an electron donating photoconductor and a boron diketonate compound.

The novel method for making the dyes of the invention is characterized by the step of reacting in stoichiometric amounts, an m-alkyl substituted tetrafluorophosphorous diketonate with an aldehyde including aldehyde derivatives such as acetals and thioformaldehyde. By m-alkyl substituted, we mean at least one alkyl group in either the 4- or 6-position of the ring. It is important that the tetrafluorophosphorous diketonate starting material have an alkyl group in either or both the 4,6-positions. Alkyl groups in these positions are activated by the tetrafluorophosphorous diketonate ring. Absence of alkyl substituents in both positions results in no reaction.

As stated above, the present invention also provides photoconductive compounds comprising a class of tetrafluorophosphorous diketonates as electron accepting sensitizers. Members of the class of diketonates have the structure:

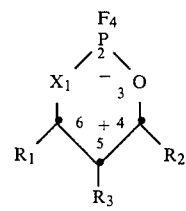

wherein $R_1$ and $R_2$ each independently represent hydrogen, alkyl, aryl, $-CH=CH_nA_1$, or $-CH=CH-CH_nA_2$;

n represents 1 or 2;

$A_1$ represents aryl, alkyl, julolyidine, arylamino, alkylamino, diarylamino or dialkylamino;

$A_2$ represents a substituted or unsubstituted tellurium-free heterocyclic nucleus generally of the type used in styryl and cyanine dyes;

$R_3$ represents hydrogen, alkyl, aryl or alkoxy; or $R_3$ together with $R_1$ or $R_2$ provides the atoms necesssary to form a fused aromatic ring such as benzoyl, benzothiozolyl and pyranyl; P X represents O, S or $NR_4$ wherein $R_4$ represents hydrogen, alkyl or aryl; or $NR_4$ together with $R_1$ and the carbon to which $R_1$ is attached forms a fused heterocyclic ring such as benzothiazole, benzoxazole and benzimidazole.

The novel methine dyes of the invention have the above structure, wherein at least one of $R_1$ and $R_2$ is $-CH=CH_nA_1$, or $-CH=CH-CH=A_2$.

Alkyl refers to straight- or branched-chained hydrocarbons having from 1 to about 20 carbon atoms including substituted or unsubstituted alkyl such as methyl, isopropyl, neopentyl, heptoyl, etc. Aryl refers to substituted and unsubstituted substituents such as phenyl or naphthyl. Substituents of aryl include hydroxy, alkyl, halogen, alkoxy, amino and nitro. Heterocyclic nuclei of the type used in styryl and cyanine dyes include substituted or unsubstituted imidazole, 3H-indole, thiazole, benzothiazole, naphthothiozole, oxazole, napthoxozole, selenozole, benzoselenazole, thiazoline, quinoline, etc.

DETAILED DESCRIPTION OF THE INVENTION

The previously mentioned method of Brown and Bladon was used to make a number of useful tetrafluorophosphorous diketonate ring compounds.

The Brown and Bladon method was also used to make the meta-alkyl substituted tetrafluorophosphorous diketonate starting materials used in the method of this invention for making the methine dyes. The method of the present invention involves the reaction of a meta-alkyl tetrafluorophosphorous diketonate compound which may be formed by the Brown and Bladon method with an aldehyde. This reaction is carried out by combining the aldehyde and the tetrafluorophosphorous diketonate in a solvent such as acetic anhydride or a high boiling water miscible solvent such as 1,2,3-trichloropropane and heating for a period of about 0.5 to 2 hours. After the reaction is complete, the reaction mixture is chilled where upon the methine dye having the tetrafluorophosphorous diketonate component can be collected and optionally washed with liquids such as ether, benzene, toluene and alcohol.

Useful aldehyde starting materials include p-dimethylaminobenzaldehyde, dimethylformamide, 9-formyljulolidine, thiophene-2-aldehyde, benzaldehyde, anisaldehyde, vanillin, veratraldehyde, syringaldehyde, cinnamaldehyde, p-dimethylaminocinnamaldehyde, pyrrole-2-aldehyde, etc. Other useful aldehydes, including the corresponding acetals and thioaldehydes, include:

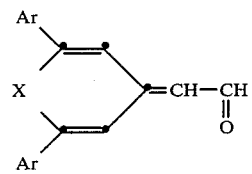

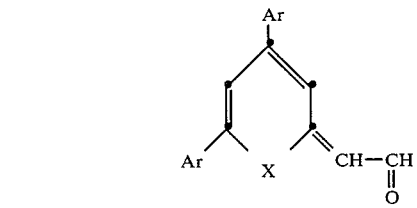

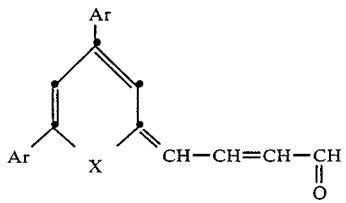

and

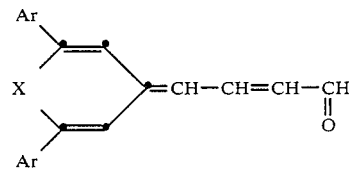

wherein
X represents O or S;
Ar represents aryl such as phenyl, naphthyl, etc.
The aldehyde may also include a heterocyclic nucleus of the type used in stryryl and cyanine dye mentioned herein before.

Representative tetrafluorophorous diketonate ring compounds, and the novel methine dyes made according to the method of this invention are presented in Table I.

TABLE I

Phosphorous Diketonates

| No. | Compound |
|---|---|
| 1 | C₆H₅ — (ring) — C₆H₅, O—PF₄—O |
| 2 | CH₃ — (ring) — CH₃, O—PF₄—O |
| 3 | C₆H₅ — (ring) — CH₃, O—PF₄—O |
| 4 | HO—C₆H₄— (ring) —C₆H₄—OCH₃, O—PF₄—O |

TABLE I-continued
Phosphorous Diketonates
| No. | Compound |
|---|---|
| 5 | 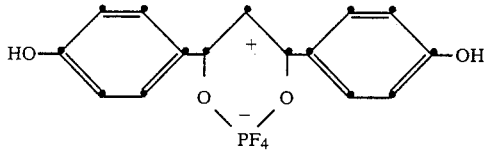 |
| 6 | 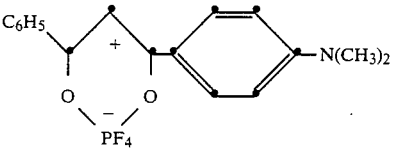 |
| 7 | 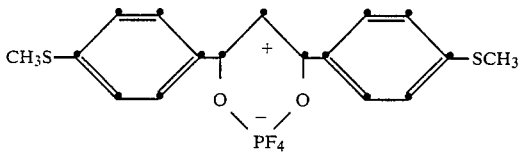 |
| 8 | 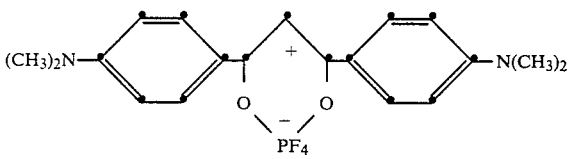 |
| 9 | 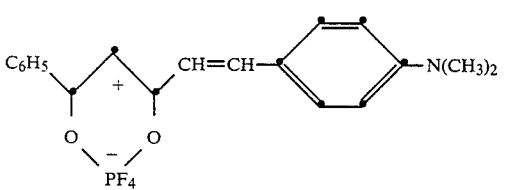 |
| 10 | 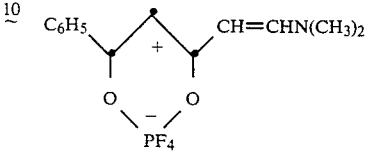 |
| 11 | 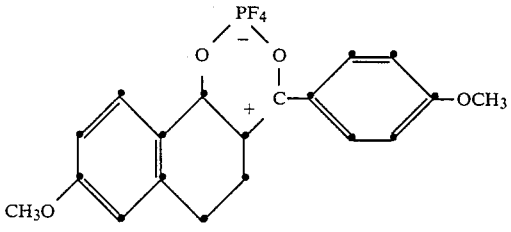 |
| 12 | 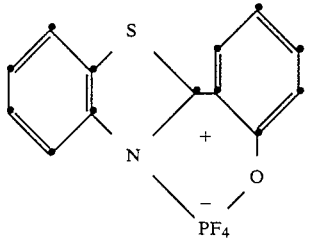 |

TABLE I-continued
Phosphorous Diketonates

| No. | Compound |
|---|---|
| 13 | (CH₃)₂N—C₆H₄—CH=CH—C(O)—CH(+)—C(O)—CH=CH—C₆H₄—N(CH₃)₂ ; PF₄⁻ bridging the two O |
| 14 | Julolidine—CH=CH—C(O)—CH(+)—C(O)—CH=CH—julolidine ; PF₄⁻ bridging |
| 15 | C₆H₅—C(O)=CH—C(CH₃)=N(+)—C₆H₅ ; PF₄⁻ bridging O and N |
| 16 | (CH₃)₂N—C₆H₄—(CH=CH)₂—C(O)—CH(+)—C(O)—(CH=CH)₂—C₆H₄—N(CH₃)₂ ; PF₄⁻ bridging |
| 17 | [3-phenyl-1-(substituted)pyranyl]—CH=CH—C(O)—CH(+)—C(O)—CH=CH—[3-phenyl-1-(substituted)pyranyl] ; PF₄⁻ bridging |
| 18 | (CH₃)₂NCH=CH—C(O)—CH(+)—C(O)—CH=CHN(CH₃)₂ ; PF₄⁻ bridging |
| 19 | CH₃O—C₆H₄—C(O)—CH(+)—C(O)—C₆H₄—OCH₃ ; PF₄⁻ bridging |

Other useful methine dyes which could be made by the novel method of this invention are presented in Table II:

TABLE II
Compound No.
(20)
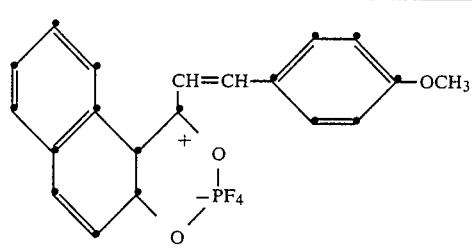
(21)
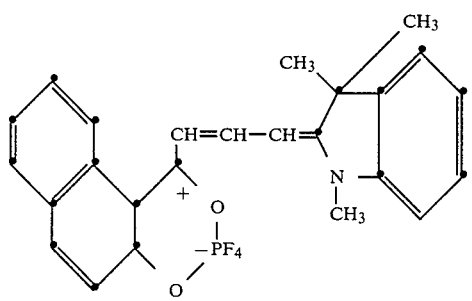
(22)
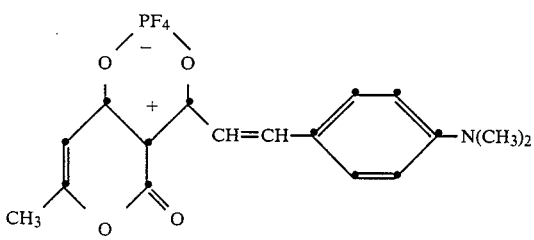
(23)
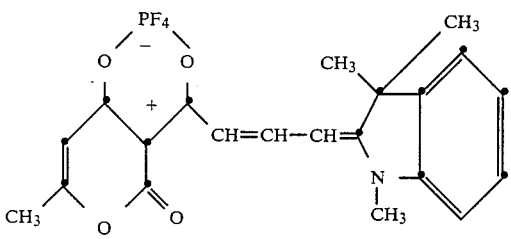
(24)
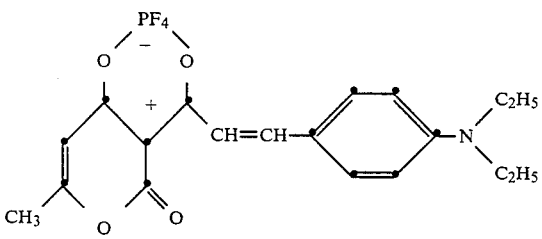
(25)
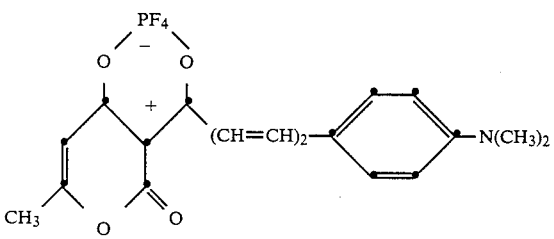

TABLE II-continued

Compound No.

(26)
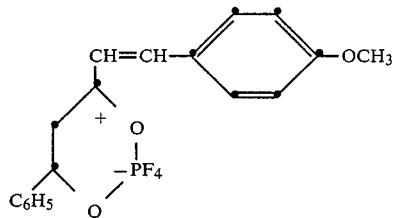

(27)
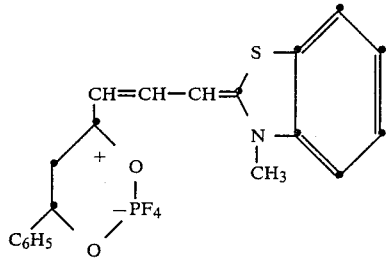

(28)
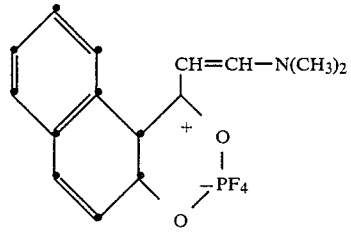

(29)
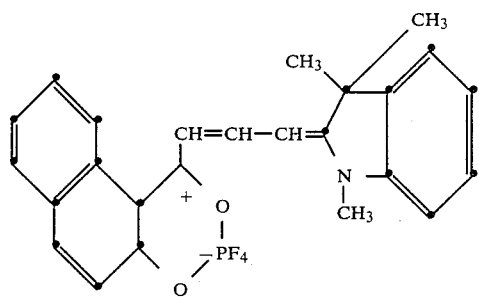

Useful electron donating photoconductors are selected from materials designated as p-type organic photoconductors in the patent literature, such as those disclosed in U.S. Pat. No. 3,615,414; U.S. Pat. No. 3,873,311; U.S. Pat. No. 3,873,312; U.S. Pat. No. 4,111,693; and Research Disclosure, 10938, Volume 109, May, 1973. These disclosures are expressly incorporated herein by reference. Especially useful electron donors are compounds which are triaryl amines or include a triarylamine component, such as tri-p-tolylamine and (di-p-tolylaminophenyl)cyclohexane. Polymeric organic photoconductors, such as polyvinylcarbazole, are also useful.

In general, the electron donating organic photoconductors are present in the composition in an amount equal to at least about 1 weight percent of the coating composition on a dry basis. The upper limit in the amount of electron donor substance present can be widely varied in accordance with usual practice. It is preferred that the electron donor be present, on a dry basis, in an amount of from about 1 weight percent of the coating composition to the limit of its solubility in the polymeric binder. A particularly preferred weight range for the electron donor in the coating composition is from about 10 weight percent to about 40 weight percent on a dry basis.

In general it is desirable to include a binder in the compositions of the invention. Materials which are employed as binders are film-forming polymeric materials having a fairly high dielectric strength and good electrically insulating properties. Such binders include styrene-butadiene copolymers; polyvinyl toluene-styrene copolymers; styrene-alkyl resins; silicone-alkyl resins; soyaalkyl resins; vinylidene chloride-vinyl chloride copolymers; poly(vinylidene chloride); vinylidene chloride-acrylonitrile copolymers; vinyl acetate vinyl chloride copolymers; poly(vinyl acetals), such as poly(vinyl butyral); nitrated polystyrene; polymethylstyrene, isobutylene polymers; polyesters, such as poly[ethylene-co-alkylenebis(alkyleneoxyaryl) phenylenedicarboxylate]; phenolformaldehyde resins; ketone resins; polyamides; polycarbonates; polythiocarbonates; poly[ethylene-co-isopropylidene-2,2-bis(ethyleneoxyphenylene)terephthalate]; copolymers of vinyl haloarylates and vinyl acetate such as poly(vinyl-m-bromobenzoate-co-vinyl acetate) and chlorinated poly(olefins), such as chlorinated poly(ethylene). Other types of binders which are useful include such materials as paraffin, mineral waxes, etc. Combinations of binder materials are also useful.

Useful results are obtained by using the selected tetrafluorophosphorous diketonates in an amount of about 0.001 to about 30 percent by weight of the photoconductive coating composition. When the tetrafluorophosphorous diketonate is used in combination with a boron diketonate the relative amounts of each is unimportant so long as the combination is sensitizing. However, in some cases amounts outside of the above range will be useful. The upper limit in the sensitizing amount of the combination in a sensitized layer is determined as a matter of choice and the total amount of any sensitizer used varies widely depending on, among other considerations, the sensitizer selected, the electrophotographic response desired, the proposed structure of the photoconductive element and the mechanical properties desired in the element.

Suitable support materials for forming elements comprising layers of the photoconductive compositions of this invention include any of a wide variety of electrically conducting supports, such as paper (at a relative humidity of about 20 percent); aluminum-paper laminates; metal foils, such as aluminum, copper, zinc, brass and galvanized plates; vapor-deposited metal layers, such as silver, chromium, nickel, aluminum, cermet materials and the like coated on paper or conventional photographic film bases, such as cellulose acetate or polystyrene. Such conducting materials as nickel are vacuum deposited on transparent film supports in sufficiently thin layers to allow electrophotographic elements prepared therewith to be exposed from either side of such elements. An especially useful conducting support is prepared by coating a support material, such as poly(ethylene terephthalate) with a conducting layer containing a semiconductor dispersed in a resin. Such conducting layers both with and without insulating barrier layers are described in U.S. Pat. No. 3,245,833 and U.S. Pat. No. 3,880,657. Likewise, a suitable conducting coating is prepared from the sodium salt of a carboxyester lactone of maleic anhydride and a vinyl acetate polymer. Such conducting layers and methods for their optimum preparation and use are disclosed in U.S. Pat. No. 3,007,901 and U.S. Pat. No. 3,262,807.

The photoconductive compositions of this invention are optionally coated directly on a conducting substrate. In some cases, it is desirable to use one or more intermediate subbing layers between the conducting substrate and coating to improve adhesion of the coating to the conducting substrate and/or to act as an electrical barrier layer between the coated composition and the conducting substrate. Such subbing layers, if used, generally have a dry thickness in the range of about 0.1 to about 5 microns. Subbing layer materials which are used are described, for example, in U.S. Pat. No. 3,143,421; U.S. Pat. No. 3,640,708 and U.S. Pat. No. 3,501,301.

Overcoat layers are useful in the present invention, if desired. For example, to improve surface hardness and resistance to abrasion, the coated layer of the element of the invention is overcoated with one or more electrically insulating, organic polymer coatings or electrically insulating, inorganic coatings. A number of such coatings are well known in the art and accordingly, extended discussion thereof is unnecessary. Useful such overcoats are disclosed, for example, in *Research Disclosure*, 10938, "Electrophotographic Elements, Materials, and Processes," Volume 109, page 63, Paragraph V, May, 1973, which is incorporated herein by reference.

Coating thicknesses of the photoconductive composition on the support vary widely. Generally, a coating in the range of about 0.5 micron to about 300 microns before drying is useful for the practice of this invention. The preferred range of coating thickness is found to be in the range from about 1.0 micron to about 150 microns before drying, although useful results can be obtained outside of this range. The resultant dry thickness of the coating is preferably between about 2 microns and about 50 microns, although useful results are obtained with a dry coating thickness between about 1 and about 200 microns.

The elements formed from the support and the photoconductive compositions of the present invention are employed in any of the well-known electrophotographic processes which require photoconductive layers. One such process is the xerographic process. In a process of this type, a photoconductive element is held in the dark and given a blanket electrostatic positive or negative charge by treating it with a corona discharge. This uniform charge is retained by the layer because of the substantial dark insulating property of the layer, i.e., the low electrical conductivity of the layer in the dark. The electrostatic charge formed on the surface of the photoconductive layer is then selectively dissipated from the surface of the layer by imagewise exposure to UV, visible or infrared radiation. Front surface exposure, rear surface exposure in the case of a transparent electrode and contact-printing projection of an image are among the specific exposure techniques by which a latent electrostatic image is formed in the photoconductive layer.

The latent electrostatic image produced by exposure is developed or transferred to another surface and developed there, i.e., either the charged or uncharged areas are rendered visible, by treatment with a medium comprising electrostatically responsive particles having optical density (electroscopic toners). The developing electrostatically responsive particles are in the form of dust, i.e., powder, or a pigment in a resinous carrier, i.e., toner.

Liquid development of the latent electrostatic image formed on the elements of this invention is preferred. In liquid development, the developing particles (electroscopic toners) are carried to the image-bearing surface in an electrically insulating liquid carrier. Methods of development of this type are widely known and have been described in the patent literature, for example, Metcalfe et al, U.S. Pat. No. 2,907,674 issued Oct. 6, 1959.

The following examples are representative of the above described novel method for preparing the methine dyes of the invention.

EXAMPLE 1

Preparation of Compound 9, Table I A mixture of 0.5 g (2 mmoles) of compound 3, (Table I) made according to the method of Brown and Bladon, 0.3 g (2 mmoles) of dimethylaminobenzaldehyde and 2 ml of acetic anhydride was heated on a steam bath for 2 hours. After chilling the reaction mixture, the solid was collected, washed with ether and dried. Melting point 235°–236° C.

EXAMPLE 2

Preparation of Compound 10, Table I A mixture of 0.5 g (2 mmoles) of compound 3, (Table I) 0.3 g (2.5 mmol) of the dimethylacetal of dimethylformamide and 1 ml of dimethylformamide was heated on a steam bath for 2 hours, chilled, and the solid was collected and washed with ether. Melting point 215°–216° C.

EXAMPLES 3–18

The following examples illustrate the use of the dyes, of the present invention as sensitizers in electrophotographic elements. Each film was formulated and coated as follows. Specific amounts of a dye sensitizer from Table I and tri-p-tolylamine were dissolved in dichloromethane. A Lexan 145 dichloromethane solution was added to the dye sensitizer tri-p-tolylamine-dichloromethane solution. Lexan 145 is a polycarbonate available from General Electric. The solution was stirred for several minutes and then coated at 0.006 mil wet thickness on a poly(ethylene terephthalate) support containing 0.4 OD evaporated nickel. After initial evaporation of the solvent, the films were dried 24 hours in air at 60° C. Dry thickness was about 7 μm. Sufficient amounts of the dye sensitizer, tri-p-tolyamine and Lexan 145 were used to prepare coated film containing 1.0 weight percent dye sensitizer, 30% tri-p-tolylamine and 69% Lexan 145.

The quantum efficiency ($\Phi_o$) of each film was measured as follows. Samples were corona-charged to a surface potential equivalent to the field strengths, $E_o$, indicated in Table II. They were then exposed to monochromatic radiation at a wavelength indicated in Table III with a bandwidth of 10 nm. The incident photon flux was measured with an Optronics Laboratories Model 730-A Radiometer. Films were allowed to discharge while exposed. The initial quantum efficiency ($\Phi_o$) (the number of electron-hole pairs pairs produced per incident photon) at field strength $E_o$ was then determined by computation of the slope of the discharge curve at $E_o$. The photodischarge sensitivity ($S_{\frac{1}{2}}$), was also determined by allowing the films to discharge from $E_o$ to $E_o/2$. The amount of radiation necessary to produce this discharge was then calculated from the time required for this half-decay and the incident photon flux.

Dyes 1–6, 9–16 and 18–19 of Table I were tested as described above. Each of the dyes resulted in an increase in the speed and/or quantum efficiency of the photoconductive layers in which they were included. The quantitative results are presented in Table III below.

TABLE III

Quantum Efficiencies and Photosensitivities for Lexan - 30%-Tri-p-tolylamine Films Containing 1% Phosphorus Diketonates-Positive Charging Front Surface Exposure

| Example No. | Table I Compound | Wavelength λ (nm) | $E_o$ max (volts/cm) | Quantum Efficiency at $E_o$ (charges/photon) | Photosensitivity $E_o \to E_o/2$ (ergs/cm²) |
|---|---|---|---|---|---|
|  | Control (no sensitizer) | 350 | $2.0 \times 10^6$ | 0.004 | 2000 |
| 3 | 1 | 350 | $1.4 \times 10^6$ | 0.18 | 32 |
| 4 | 2 | 350 | $5.5 \times 10^5$ | 0.014 | 97 |
| 5 | 3 | 350 | $5.6 \times 10^5$ | 0.065 | 38 |
| 6 | 4 | 350 | $2.5 \times 10^5$ | 0.062 | 23 |
| 7 | 5 at 0.5% | 430 | $6.3 \times 10^5$ | 0.05 | 59 |
| 8 | 6 | 480 | $1.4 \times 10^6$ | 0.25 | 23 |
| 9 | 9 | 375 | $1 \times 10^6$ | 0.039 | 154 |
| 10 | 10 | 410 | $4.4 \times 10^5$ | 0.070 | 36 |
| 11 | 11 | 435 | $7.5 \times 10^5$ | 0.12 | 27 |
| 12 | 12 | 350 | $1.0 \times 10^6$ | 0.046 | 109 |
| 13 | 13 | 645 | $1.4 \times 10^6$ | 0.08 | 74 |
| 14 | 14 | 710 | $1.1 \times 10^6$ | 0.007 | 527 |
| 15 | 15 | 350 | $1.4 \times 10^6$ | 0.33 | 27 |
| 16 | 16 | 660 | $5.7 \times 10^5$ | 0.0014 | 1641 |
| 17 | 18 | 455 | $3.5 \times 10^5$ | 0.0016 | 576 |
| 18 | 19 | 425 | $1.1 \times 10^6$ | 0.21 | 17 |

EXAMPLE 19

Synergistic Effect of Phosphorous Diketonate Dye on Spectral Sensitization

The addition of boron diketonate acceptors to photoconductive films containing an electron donating type of photoconductor and another boron diketonate methine dye enhances the spectral sensitization of the film. The same is true for the phosphorous diketonate acceptors, but is unexpectedly more pronounced especially for longer wavelength dyes. Table IV shows the effects of added acceptors on the spectral sensitization of a film containing the boron diketonate methine dye below with peaks at λ=680 and 735 nm. The films were prepared as in Examples 3–18. Quantum efficiency and sensitivity measurements were also carried out as in Examples 3–18.

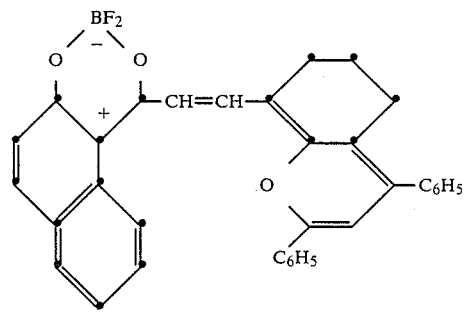

Boron Diketonate Methine Dye

The results show that the phosphorous diketonate acceptors of this invention are superior to boron diketonate acceptors in enhancing spectral sensitization beyond 600 nm of photoconductive films containing an electron donating photoconductor and a boron diketonate methine dye.

TABLE IV

Photosensitivity of Lexan 145-30%-Tri-p-Tolylamine Films Containing 2% boron Diketonate Methine Dye and 2% Phosphorous Diketonate Acceptors by Weight Front Surface Positive Charging. $E_o = 4 \times 10^5$ V/cm

| Acceptor | λ (nm) | Photosensitivity (ergs/cm$^2$) $E_o \rightarrow E_o/2$ |
|---|---|---|
| None (Control) | 680 | 12,544 ergs/cm$^2$ |
|  | 735 | >20,000 |
| (BF$_2$, O–O, F$_3$C, furan) | 680 | 10,358 |
|  | 735 | 12,880 |
| (BF$_2$, O–O, phenyl, NO$_2$-phenyl) | 680 | 5,741 |
|  | 735 | 11,230 |
| (BF$_2$, O–O, phenyl, N-CH$_3$-phenyl) | 680 | 14,495 |
|  | 735 | >20,000 |
| (BF$_2$, O–O, F$_3$C, thiophene) | 680 | 7,600 |
|  | 735 | 10,753 |
| (C$_6$H$_5$, C$_6$H$_5$, O–O, PF$_4$) | 680 | 648 |
|  | 735 | 765 |

The invention has been described in detail with particular reference to preferred embodiments thereof, but it will be understood that variations and modifications can be effected within the spirit and scope of the invention.

What is claimed is:

1. A method of making a tellurium-free dye having a tetrafluorophosphorous diketonate component comprising the step of reacting in stoichiometric amounts, an m-alkyl substituted tetrafluorophosphorous diketonate with an aldehyde.

2. The method of claim 1 wherein the aldehyde includes a component selected from the group consisting of aryl and heterocyclic nuclei.

3. The method of claim 1 wherein the aldehyde is selected from the group consisting of p-dimethylaminobenzaldehyde, dimethylformamide, julolidine aldehyde, thiophene-2-aldehyde, benzaldehyde, anisaldehyde, vanillin, veratraldehyde, syringaldehyde, cinnamaldehyde, p-dimethylaminocinnamaldehyde, and pyrrole-2-aldehyde.

4. A dye comprising a methine linking group linked to a tellurium-free tetrafluorophosphate diketonate component.

5. A methine dye comprising a tetrafluorophosphorous diketonate component having the structure:

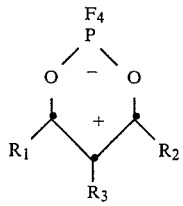

wherein
R$_1$ and R$_2$ each independently represent hydrogen, alkyl, aryl, —CH=CH$_n$A$_1$, or —CH=CH—CH-)$_n$A$_2$;
n represents 1 or 2;
A$_1$ represents aryl, alkyl, julolyidine, arylamino, alkylamino, diarylamino or dialkylamino;
A$_2$ represents a substituted or unsubstituted tellurium-free heterocyclic nucleus;
R$_3$ represents hydrogen, alky, aryl or alkoxy; or R$_3$ together with R$_1$ or R$_2$ provides the atoms necessary to form a fused aromatic ring;
provided that at least one of R$_1$ and R$_2$ is —CH=CH$_n$A$_1$, or —CH=CH—CH)A$_2$.

6. The compound of claim 5 wherein
R$_1$ and R$_2$ are each independently methyl, phenyl, methoxyphenyl, hydroxyphenyl, dimethylamino phenyl, methylthiophenyl, —CH=CH)A$_1$, or —CH=CH—CH)A$_2$;
A$_1$ represents dimethylamino, julolydine, dimethylamino, phenyl or benzo [2,4] phenylpyran, phenylmethoxy, carboxylamino, methoxyphenyl and diethylaminophenyl;
A$_2$ represents benzoazole or benzothiazole;
R$_3$ represents hydrogen or together with R$_1$ or R$_2$ form a fused pyranyl, benzoyl or benzothiazole ring.

7. A compound selected from the group consisting of

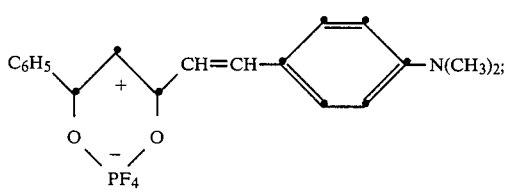

-continued
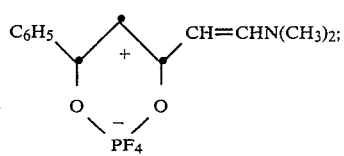
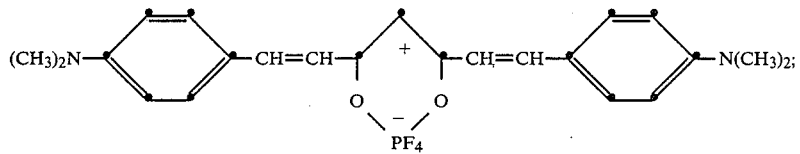
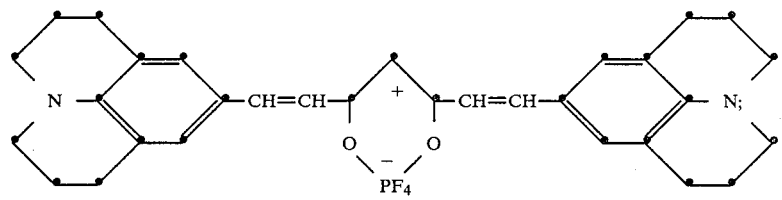
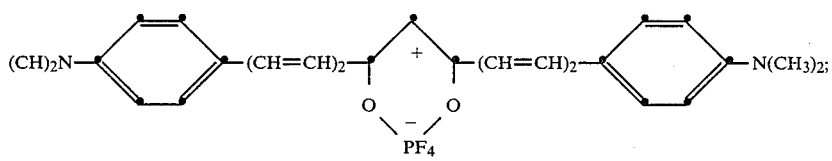
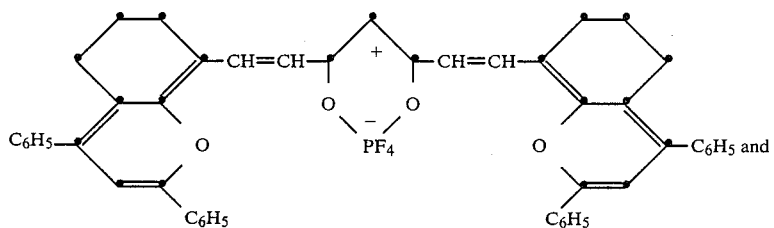
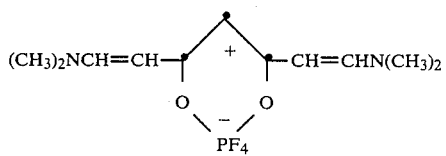
* * * * *

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below:

Col. 2, lines 15-23 the structure reading " 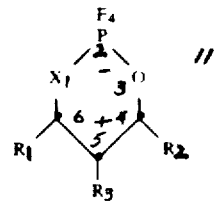 "
should read -- 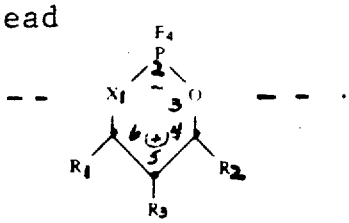 --.

Col. 2, line 26, the part reading " $-CH=CH_nA_1$, or $-CH=CH-CH_nA_2$ "
should read -- $-(CH=CH)_{\overline{n}}A_1$, or $-CH=(CH-CH)_{\overline{n}}A_2$; --.

Col. 2, line 43, the part reading " $-CH=CH_nA_1$, or $-CH=CH-CH=A_2$ "
should read -- $-(CH=CH)_{\overline{n}}A_1$, or $-CH=(CH-CH)_{\overline{n}}A_2$. --.

UNITED STATES PATENT AND TRADEMARK OFFICE
CERTIFICATE OF CORRECTION

PATENT NO. : 4,496,730

DATED : January 29, 1985

INVENTOR(S) : Chin H. Chen et al

It is certified that error appears in the above-identified patent and that said Letters Patent are hereby corrected as shown below:

Col. 4, Table I reading "

| TABLE I | |
|---|---|
| No. Compound | Phosphorous Diketonates |
| 1 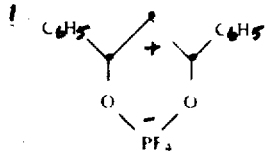 | |
| 2 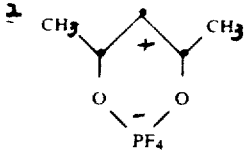 | |
| 3 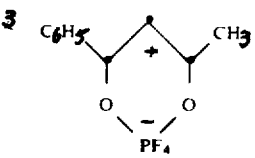 | |
| 4 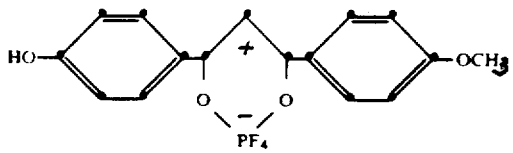 | |

"

UNITED STATES PATENT AND TRADEMARK OFFICE
CERTIFICATE OF CORRECTION

PATENT NO. : 4,496,730

DATED : January 29, 1985

INVENTOR(S) : Chin H. Chen et al

It is certified that error appears in the above-identified patent and that said Letters Patent are hereby corrected as shown below:

should read

TABLE I

Phosphorous Diketonates

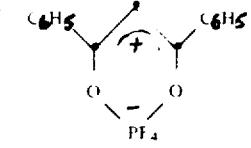

1. 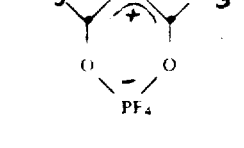

2. 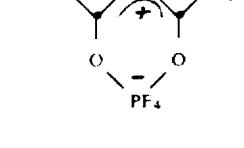

3.

4. 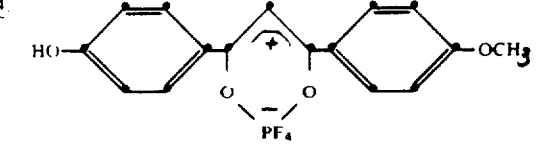

UNITED STATES PATENT AND TRADEMARK OFFICE
CERTIFICATE OF CORRECTION

PATENT NO. : 4,496,730  Page 4 of 31
DATED : January 29, 1985
INVENTOR(S) : Chin H. Chen et al It is certified that error appears in the above-identified patent and that said Letters Patent are hereby corrected as shown below:

Cols. 5 & 6, Cmpds. 5-8 reading

"

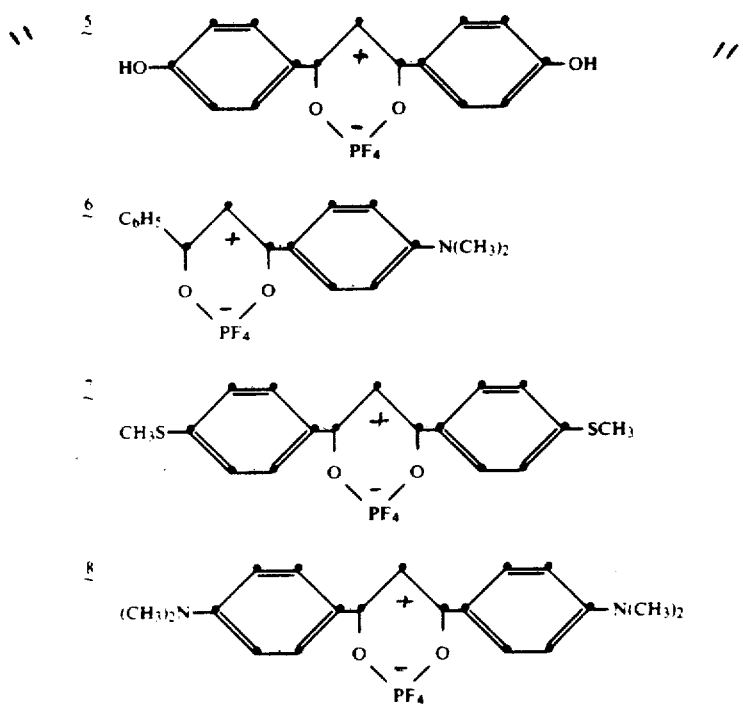

"

UNITED STATES PATENT AND TRADEMARK OFFICE
CERTIFICATE OF CORRECTION

PATENT NO. : 4,496,730

DATED : January 29, 1985

INVENTOR(S) : Chin H. Chen et al

It is certified that error appears in the above-identified patent and that said Letters Patent are hereby corrected as shown below:

should read

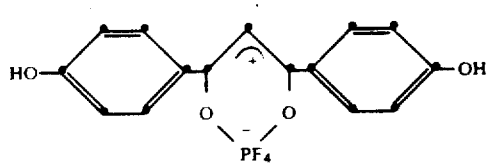

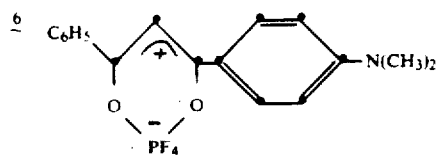

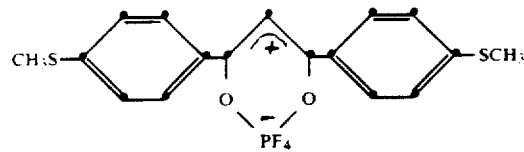

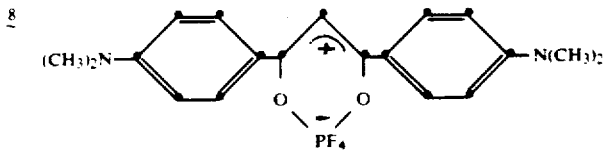

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al Page 6 of 31

It is certified that error appears in the above-identified patent and that said Letters Patent are hereby corrected as shown below:

Cols. 5 & 6, Cmpds. 9-12 reading

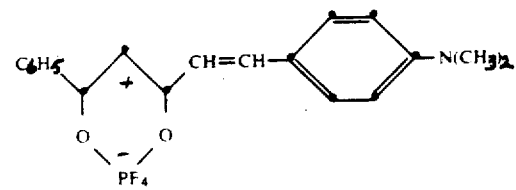
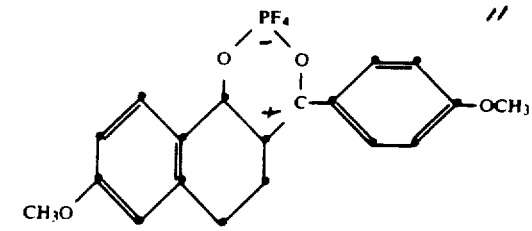
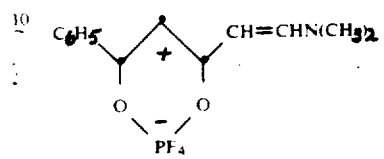
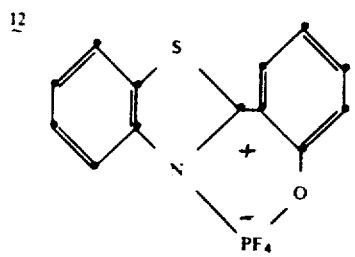

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below:

should read

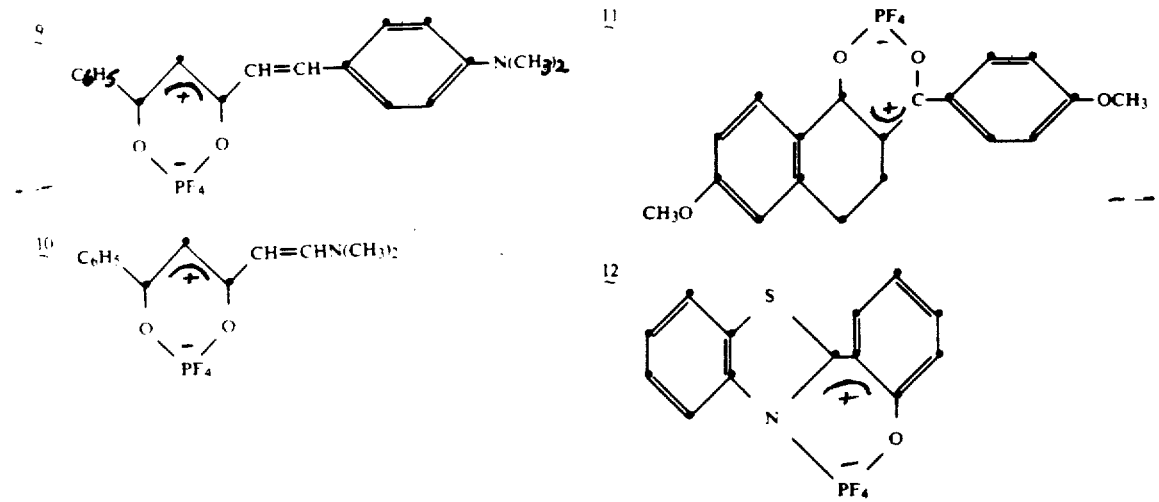

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below:

Cols. 7 & 8, Cmpds. 13-16 reading

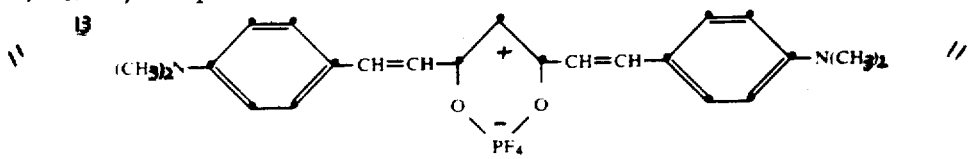

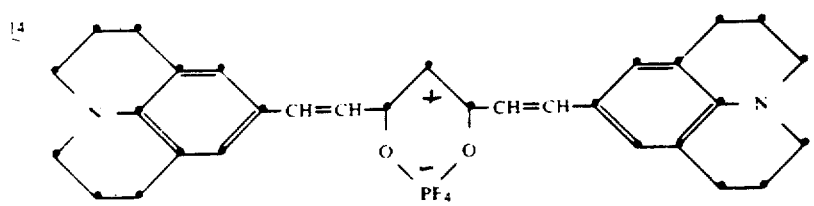

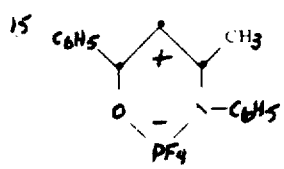

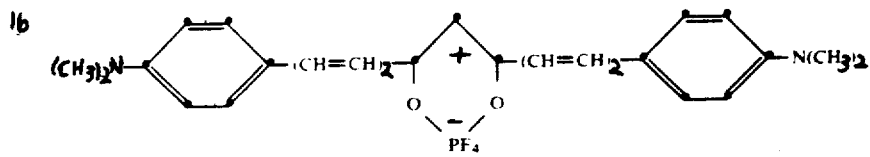

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below:

should read

13 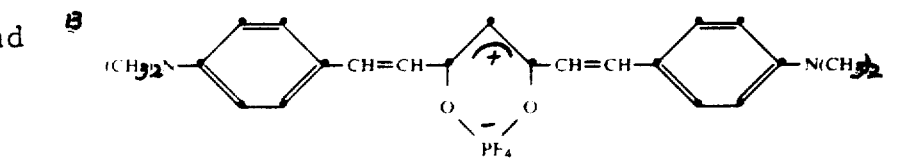

14 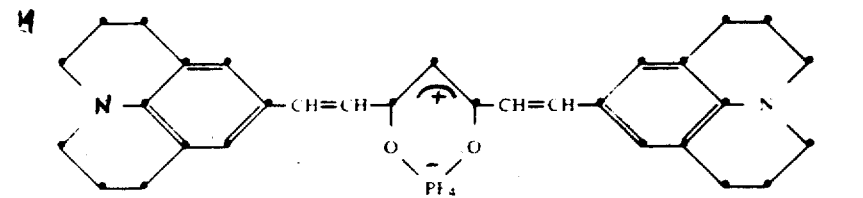

15 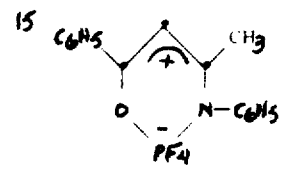

16 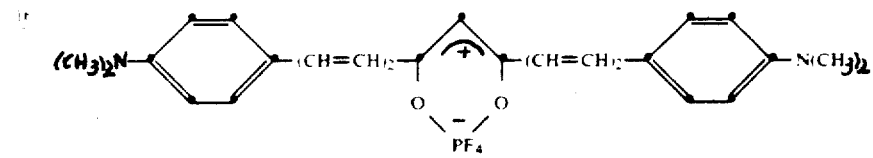

UNITED STATES PATENT AND TRADEMARK OFFICE
CERTIFICATE OF CORRECTION

PATENT NO. : 4,496,730

DATED : January 29, 1985

INVENTOR(S) : Chin H. Chen et al

It is certified that error appears in the above-identified patent and that said Letters Patent are hereby corrected as shown below:

Cols. 7 & 8, Cmpds. 17-19 reading

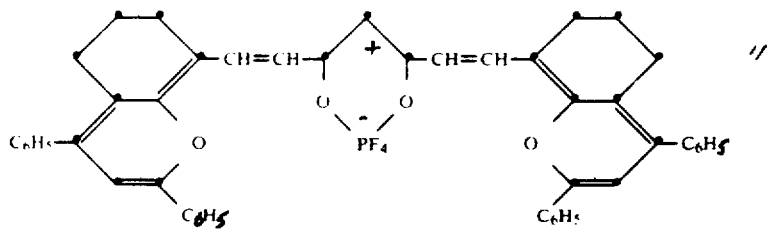

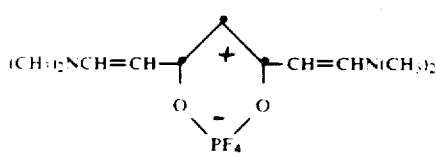

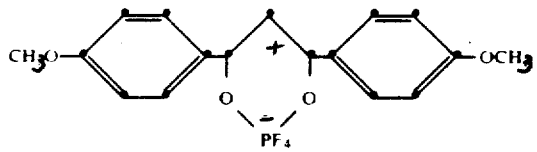

UNITED STATES PATENT AND TRADEMARK OFFICE
CERTIFICATE OF CORRECTION

PATENT NO. 4,496,730

DATED January 29, 1985

INVENTOR(S) Chin H. Chen et al

It is certified that error appears in the above-identified patent and that said Letters Patent are hereby corrected as shown below:

should read

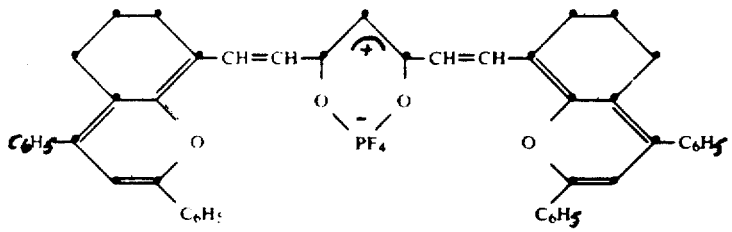

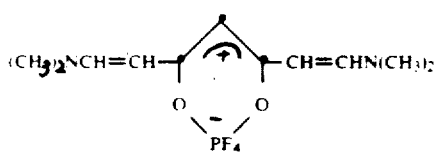

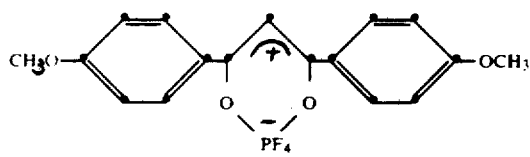

UNITED STATES PATENT AND TRADEMARK OFFICE
CERTIFICATE OF CORRECTION

PATENT NO. : 4,496,730

DATED : January 29, 1985

INVENTOR(S) : Chin H. Chen et al

It is certified that error appears in the above-identified patent and that said Letters Patent are hereby corrected as shown below:

Cols. 9 & 10, Cmpds. 20-24 reading

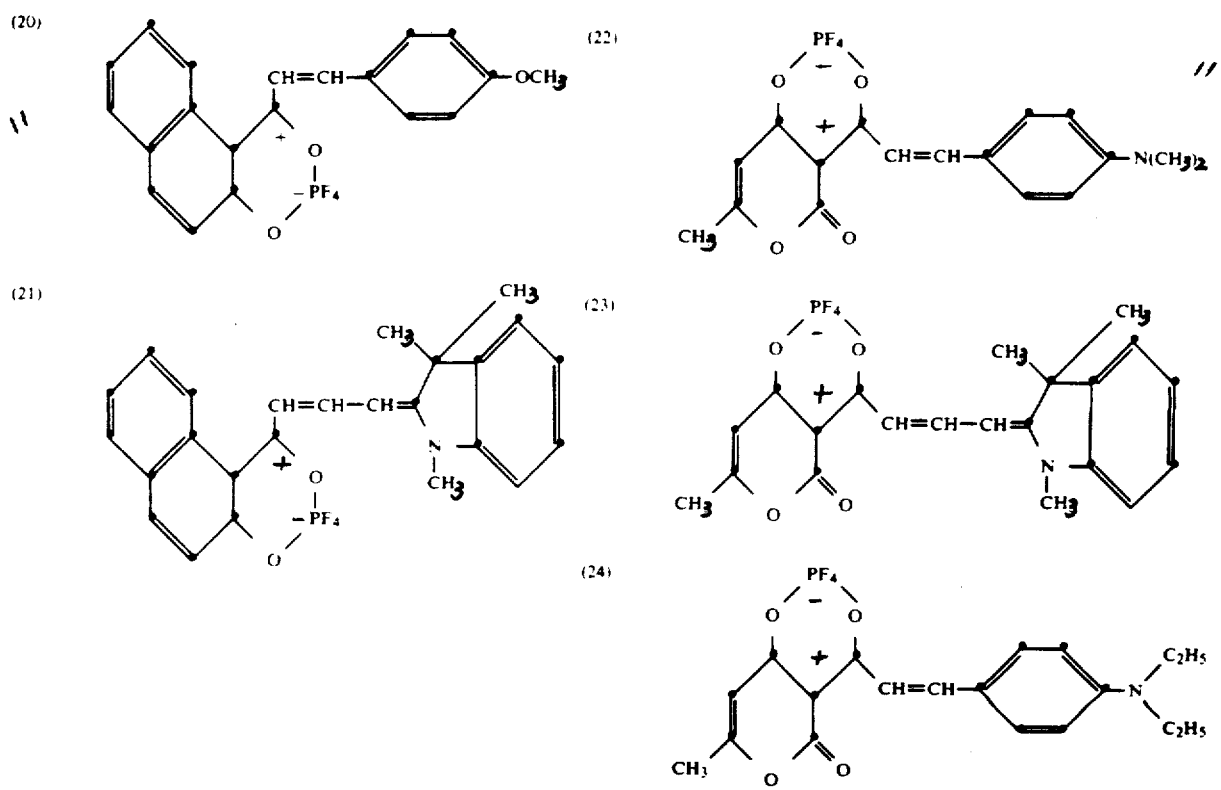

UNITED STATES PATENT AND TRADEMARK OFFICE
CERTIFICATE OF CORRECTION

PATENT NO. : 4,496,730  Page 13 of 31
DATED : January 29, 1985
INVENTOR(S) : Chin H. Chen et al It is certified that error appears in the above-identified patent and that said Letters Patent are hereby corrected as shown below Col. 9 and 10, Cmpds. 20-24 should read

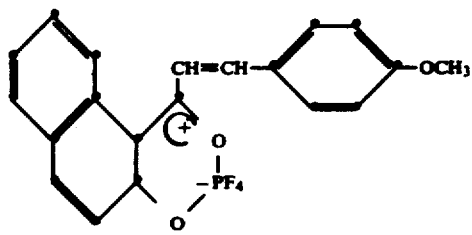
(20)

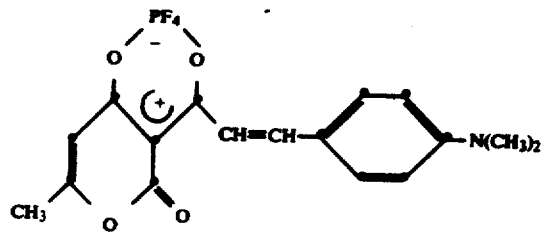
(22)

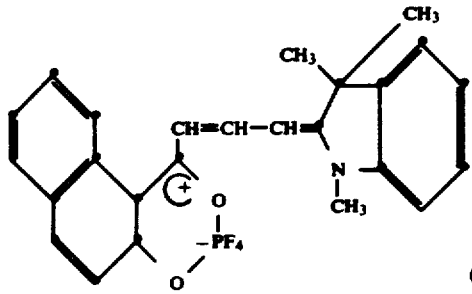
(21)

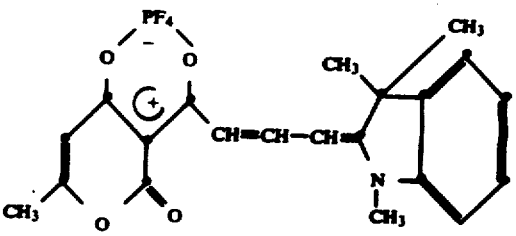
(23)

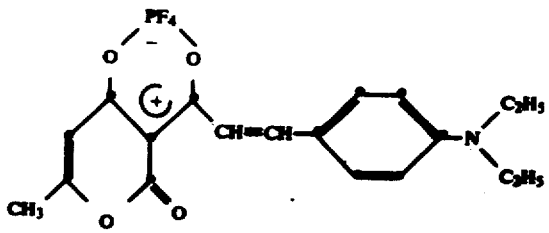
(24)

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below:

Cols. 9 & 10, Cmpd. 25 reading

"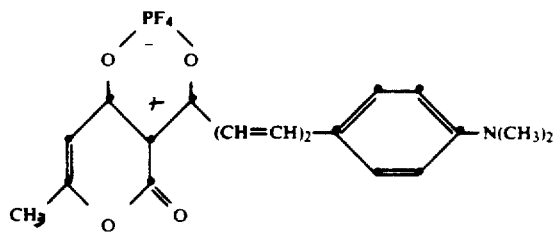"

should read

--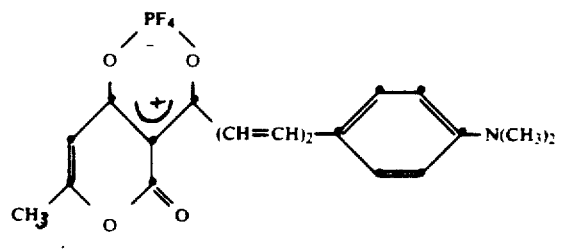--

UNITED STATES PATENT AND TRADEMARK OFFICE
CERTIFICATE OF CORRECTION

PATENT NO. : 4,496,730

DATED : January 29, 1985

INVENTOR(S) : Chin H. Chen et al

It is certified that error appears in the above-identified patent and that said Letters Patent are hereby corrected as shown below:

Col. 9 and 10, Cmpd. 25 should read

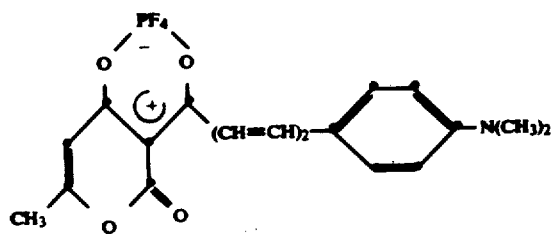

UNITED STATES PATENT AND TRADEMARK OFFICE
CERTIFICATE OF CORRECTION

PATENT NO. : 4,496,730  
DATED : January 29, 1985  
INVENTOR(S) : Chin H. Chen et al Page 16 of 31

It is certified that error appears in the above-identified patent and that said Letters Patent are hereby corrected as shown below:

Col. 11, Cmpds. 26-29 reading

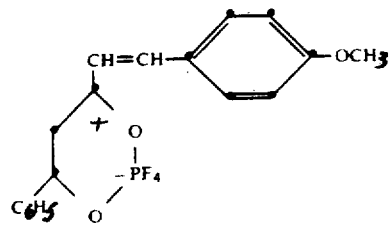
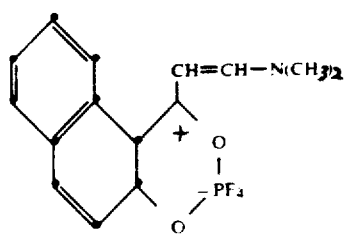
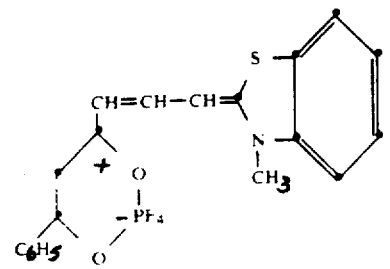
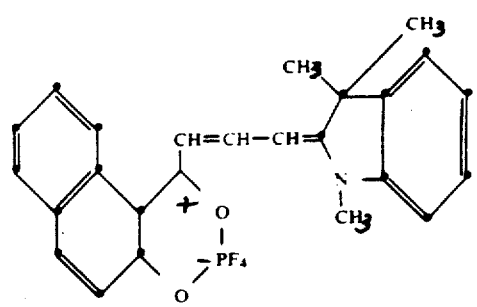

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below Col. 11, Cmpds. 26-29 should read

(26) 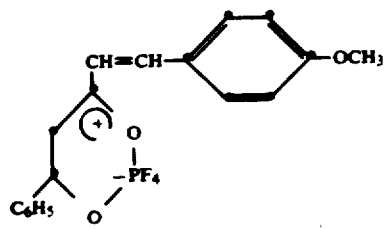

(28) 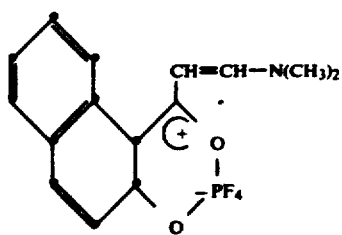

(27) 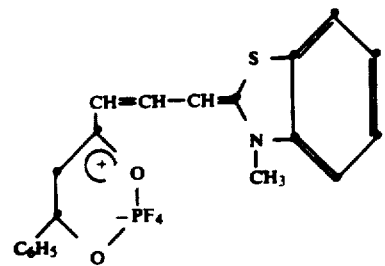

(29) 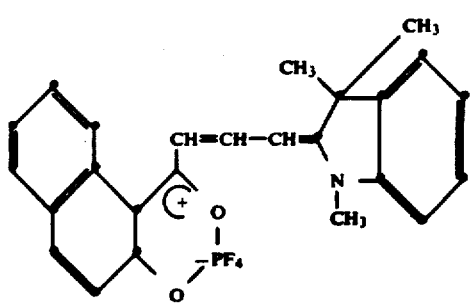

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below Col. 16, lines 48-64 reading

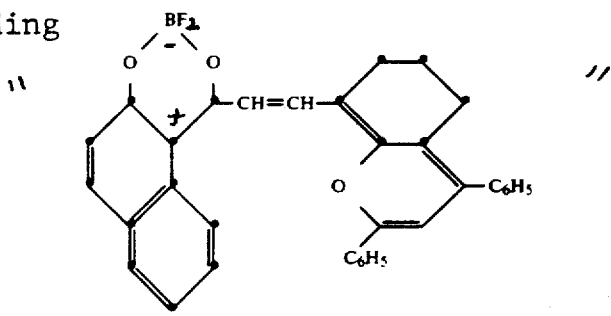

"
Boron Diketonate Methine Dye
"

should read

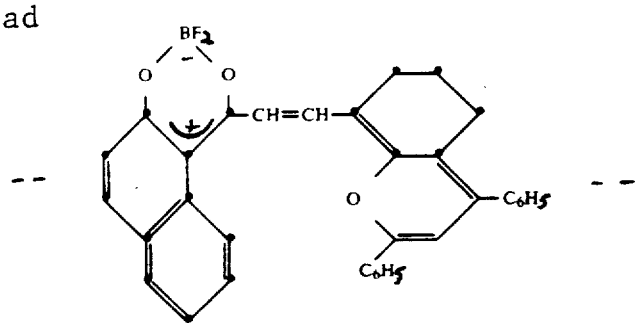

-- Boron Diketonate Methine Dye --

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below Col. 17, lines 13-26 reading "
| | | |
|---|---|---|
| None (Control) | 680 | 12.544 ergs/cm$^2$ |
| | 735 | >20,000 |
| 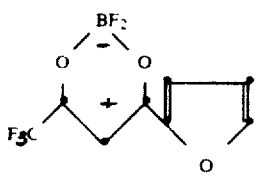 | 680 | 10,358 |
| | 735 | 12,880 |
| 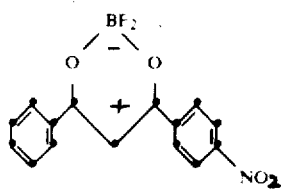 | 680 | 5,741 |
| | 735 | 11,230 |
"

UNITED STATES PATENT AND TRADEMARK OFFICE
CERTIFICATE OF CORRECTION

PATENT NO. : 4,496,730

DATED : January 29, 1985

INVENTOR(S) : Chin H. Chen et al

It is certified that error appears in the above-identified patent and that said Letters Patent are hereby corrected as shown below:

should read

| | | |
|---|---|---|
| None (Control) | 680 | 12.544 ergs/cm$^2$ |
| | 735 | >20.000 |
| 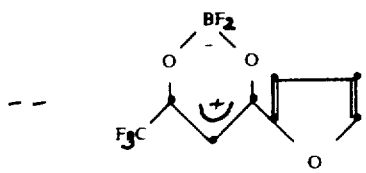 | 680 | 10.358 |
| | 735 | 12.880 |
| 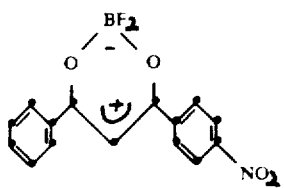 | 680 | 5.741 |
| | 735 | 11.230 |

-- -- ns UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below Col. 17, lines 27-49 reading

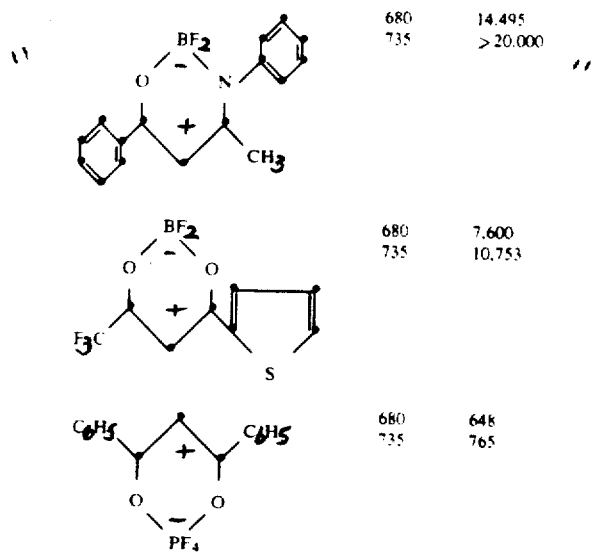

UNITED STATES PATENT AND TRADEMARK OFFICE
CERTIFICATE OF CORRECTION

PATENT NO. : 4,496,730

DATED : January 29, 1985

INVENTOR(S) : Chin H. Chen et al

It is certified that error appears in the above-identified patent and that said Letters Patent are hereby corrected as shown below:

should read

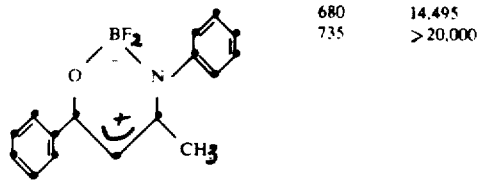   680   14,495
            735   >20,000

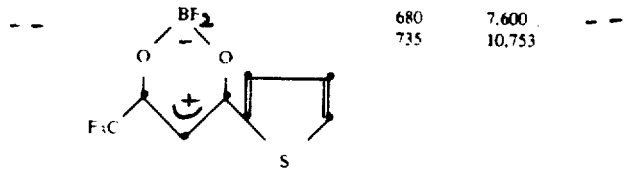   680   7,600
            735   10,753

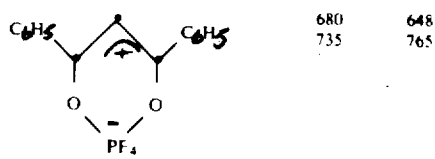   680   648
            735   765

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below:

Col. 18, lines 20-27 reading " 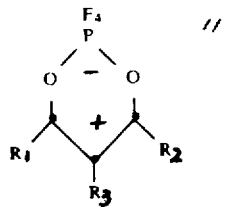 "

should read 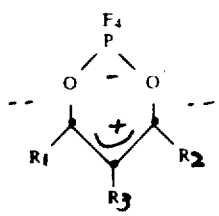

UNITED STATES PATENT AND TRADEMARK OFFICE
CERTIFICATE OF CORRECTION

PATENT NO. : 4,496,730

DATED : January 29, 1985

INVENTOR(S) : Chin H. Chen et al

It is certified that error appears in the above-identified patent and that said Letters Patent are hereby corrected as shown below:

Col. 18, lines 31-32, the part reading

" alkyl, aryl, $-CH=CH_nA_1$, or $-CH=CH-CH-)_nA_2$ "

should read --alkyl, aryl, $-(CH=CH)_nA_1$, or $-CH=(CH-CH)_nA_2$; --.

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below Col. 18, lines 41-42 reading $-CH=CH_nA_1$, or $-CH=CH-CH)A_2$ should read $-(CH=CH)_nA_1$, or $-(CH=CH-CH)A_2$.

Col. 18, lines 46-47 reading $-CH=CH)A_1$, or $-CH=CH-CH)A_2$;

should read $-(CH=CH)-A_1$, or $-(CH=CH-CH)-A_2$;.

UNITED STATES PATENT AND TRADEMARK OFFICE
CERTIFICATE OF CORRECTION

PATENT NO. : 4,496,730

DATED : January 29, 1985

INVENTOR(S) : Chin H. Chen et al

Page 26 of 31

It is certified that error appears in the above-identified patent and that said Letters Patent are hereby corrected as shown below Col. 18, last structure reading

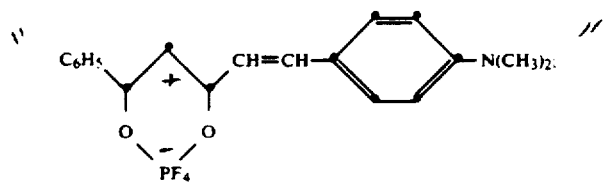

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below:

should read

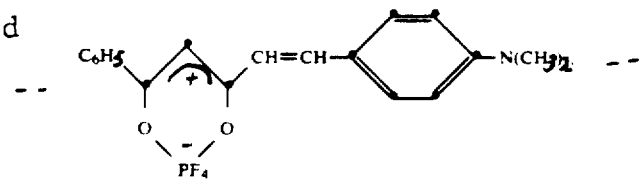

UNITED STATES PATENT AND TRADEMARK OFFICE
CERTIFICATE OF CORRECTION

PATENT NO. : 4,496,730  
DATED : January 29, 1985  
INVENTOR(S) : Chin H. Chen et al Page 28 of 31

It is certified that error appears in the above-identified patent and that said Letters Patent are hereby corrected as shown below:

Col. 19 & 20, lines 1-14 reading

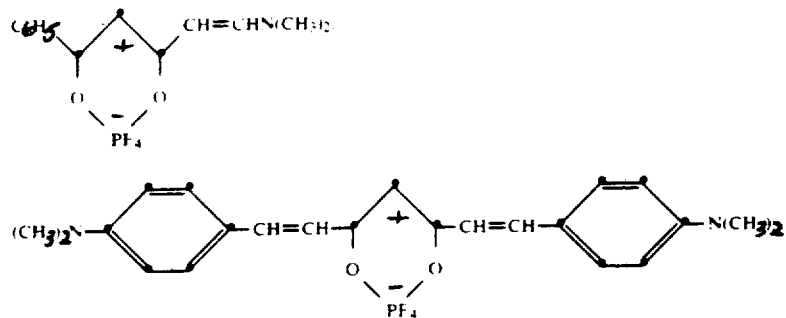

UNITED STATES PATENT AND TRADEMARK OFFICE
CERTIFICATE OF CORRECTION

PATENT NO. : 4,496,730
DATED : January 29, 1985
INVENTOR(S) : Chin H. Chen et al It is certified that error appears in the above-identified patent and that said Letters Patent are hereby corrected as shown below should read

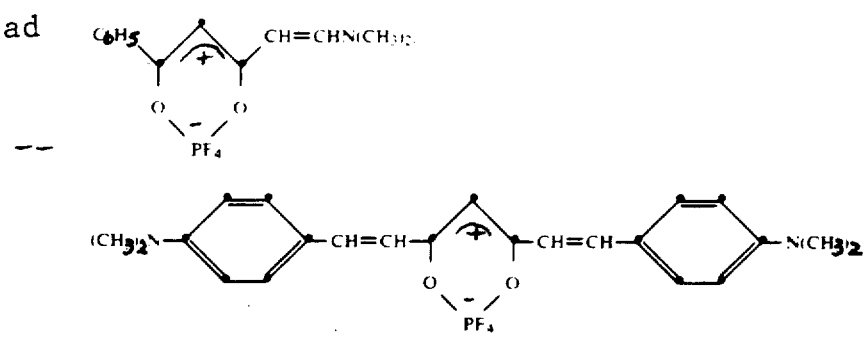

UNITED STATES PATENT AND TRADEMARK OFFICE
CERTIFICATE OF CORRECTION

PATENT NO. 4,496,730  
DATED January 29, 1985  
INVENTOR(S) Chin H. Chen et al

It is certified that error appears in the above-identified patent and that said Letters Patent are hereby corrected as shown below Cols. 19 & 20, lines 16-48 reading

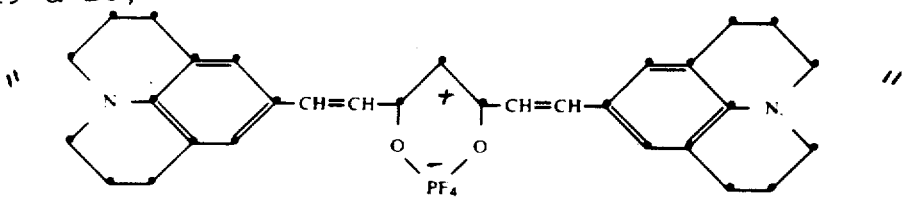

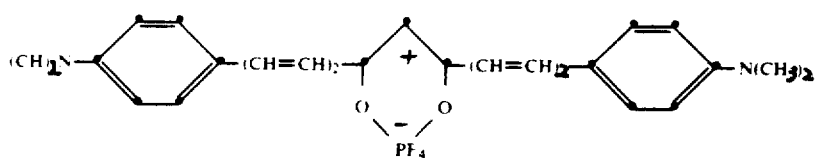

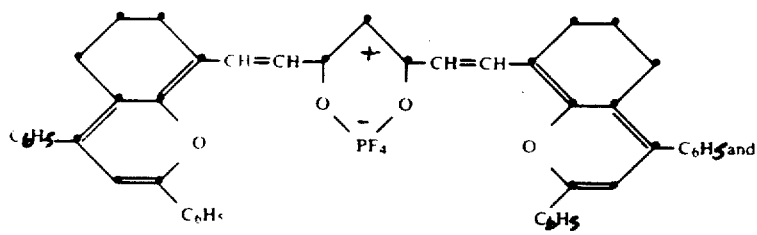

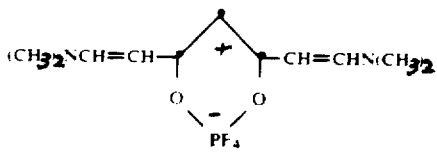

should read

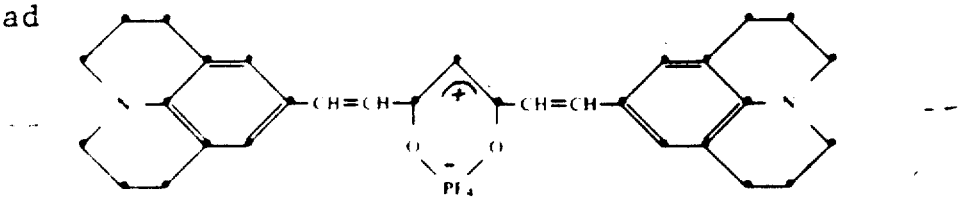

UNITED STATES PATENT AND TRADEMARK OFFICE
CERTIFICATE OF CORRECTION

PATENT NO. : 4,496,730

DATED : January 29, 1985

INVENTOR(S) : Chin H. Chen et al

It is certified that error appears in the above-identified patent and that said Letters Patent are hereby corrected as shown below

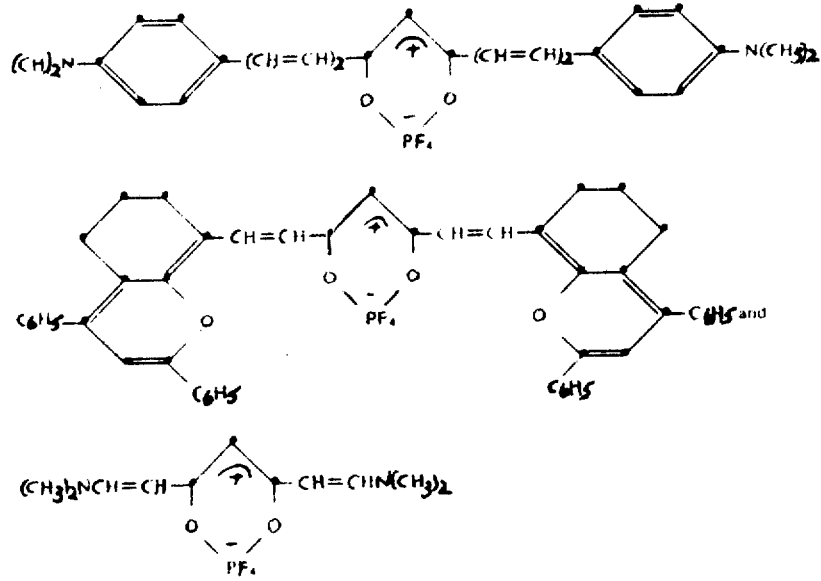

Signed and Sealed this

Seventeenth Day of December 1985

[SEAL]

Attest:

DONALD J. QUIGG

Attesting Officer

Commissioner of Patents and Trademarks